(12) United States Patent
Arkles et al.

(10) Patent No.: US 6,642,403 B2
(45) Date of Patent: Nov. 4, 2003

(54) SILICON-BASED BLOCKING AGENTS SUITABLE FOR FLUOROUS PHASE SYNTHESIS

(75) Inventors: Barry C. Arkles, Dresher, PA (US); Youlin Pan, Langhorne, PA (US); Gerald L. Larson, Newtown, PA (US)

(73) Assignee: Gelest, Inc., Morrisville, PA (US)

( * ) Notice: Subject to any disclaimer, the term of this patent is extended or adjusted under 35 U.S.C. 154(b) by 0 days.

(21) Appl. No.: 10/288,815

(22) Filed: Nov. 6, 2002

(65) Prior Publication Data

US 2003/0092927 A1 May 15, 2003

Related U.S. Application Data

(60) Provisional application No. 60/338,003, filed on Nov. 7, 2001.

(51) Int. Cl.[7] .................................................. C07F 7/04
(52) U.S. Cl. ...................... 556/451; 556/452; 556/453; 556/454
(58) Field of Search ................................ 556/451, 452, 556/453, 454

(56) References Cited

PUBLICATIONS

D.P Curran. *Angew Chem Int'l Ed.*, 37, pp. 1174–1196 (1998).

*Primary Examiner*—Samuel Barts
(74) *Attorney, Agent, or Firm*—Akin, Gump, Strauss, Hauer & Feld, L.L.P.

(57) ABSTRACT

This invention relates to a series of fluoroalkylsilane compounds of formula I.

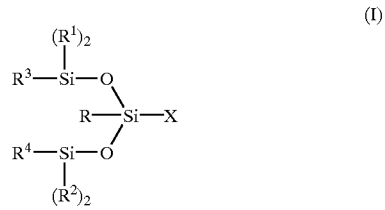

These compounds are silylation reagents which enhance the solubility of the silylated products in fluorocarbon solvents for preferred use in fluorous phase synthesis. Use of these compounds protects fragile hydrogen groups and also provides for the straightforward separation of the ultimate reaction products though fluorous phase extraction. This invention also relates to a two-step process for making compounds of formula I. The process comprises reacting an alkyldialkoxysilane with a perfluoroalkyl-substituted silane to produce a perfluoroalkyl-substituted dialkylsiloxyalkylsilane intermediate; and reacting the intermediate with halogen.

9 Claims, No Drawings

SILICON-BASED BLOCKING AGENTS SUITABLE FOR FLUOROUS PHASE SYNTHESIS

CROSS-REFERENCE TO RELATED APPLICATION

This application claims the benefit of U.S. Provisional Application No. 60/338,003, filed Nov. 7, 2001.

BACKGROUND OF THE INVENTION

Silylation is a process whereby a silyl group, typically a trimethylsilyl group, is introduced into a molecule, usually in substitution for an active hydrogen. Silylation is often part of a synthetic or analytic strategy in which a protic hydrogen of the type found in alcohols or amines is replaced in order to proceed in a synthetic step in which the hydrogen would otherwise interfere, or in order to make the molecule more volatile or more soluble in an organic solvent.

A goal of synthetic chemists is not only to synthesize new compounds, but also to be able to purify the new materials. Purification first involves the separation of the desired product from the reaction mixture and from various byproducts, which can be accomplished by methods such as evaporation, filtration and extraction. Ideally, only the desired product is soluble in a particular phase, and thus can be easily extracted. Typical phases used in separation are gas, liquid (organic and aqueous), and solid. A less common phase, the fluorous liquid phase, is becoming increasingly more utilized in synthetic chemistry as a means of separation, and it is this phase which relates to the present invention.

The fluorous phase is a phase comprising highly fluorinated solvents and compounds that dissolve in them. Perfluorocarbon and some very highly fluorinated liquids are nonpolar and nontoxic, and are immiscible with many common organic solvents and water. Because organic and inorganic compounds have little or no tendency to dissolve in the fluorous phase, it is very useful for extracting fluorous compounds.

For this reason, there has recently been considerable interest in "fluorous phase synthesis." In fluorous synthesis, a fluorous phase label is attached to a substrate such that the labeled substrate and resulting products will be separable into the fluorous phase using a separation technique such as fluorous-organic liquid-liquid extraction. The substrate is then subjected to one or more reactions before the fluorous label is removed, yielding the desired small molecule. (D. P. Curran. *Angew. Chem. Int'l Ed.*, 37, pp. 1174–1196 (1998), which is incorporated herein by reference.)

Fluorous synthesis is attractive for several reasons. First, the tagged molecule containing the fluorous label can be separated from untagged molecules using straightforward liquid-liquid or solid-phase extraction methods. Second, perfluoroalkyl chains are quite stable under organic reaction conditions, and thus tagged molecules containing fluorous labels can be exposed to a range of reaction conditions. Additionally, because fluorous labels can be attached and detached at the same site, the labels can be easily recycled. Finally, the substrates utilized in fluorous synthesis are soluble and thus can be identified and analyzed by analytical techniques which are typically utilized for the analysis of small molecules.

However, despite such advantages, there remains a need in the art for silylation reagents which would be suitable for fluorous phase synthesis for silylation reactions by rendering the silylated compounds soluble in fluorocarbon solvents. Such silylation reagents should have the same requirements in a reactivity sense to those used in conventional syntheses, however, there is also a need for an additional solubility in fluorous phases.

SUMMARY OF THE INVENTION

This invention relates to a series of fluoroalkylsilane compounds designated by the Formula I, wherein $R^1$ and $R^2$ are independently selected from the group consisting of hydrogen and lower alkyl groups of from about 1 to 5 carbon atoms; $R^3$ is $R^1R^5$ wherein $R^5$ is any branched or straight chain perfluoroalkyl of from about 1 to 25 carbon atoms; $R^4$ is $R^1R^6$ wherein $R^6$ is any branched or straight chain perfluroalkyl of from about 5 to 25 carbon atoms; R is selected from the group consisting of linear and branched alkyl groups; and X is a hydrolyzable group or atom.

This invention also relates to a process for producing the compound of Formula (I), comprising reacting an alkyl-dialkoxysilane with a perfluoroalkyl-substituted silane to produce a perfluoroalkyl-substituted dialkylsiloxyalkylsilane intermediate; and reacting the intermediate with halogen.

DETAILED DESCRIPTION OF THE INVENTION

This invention relates to a series of fluoroalkylsiloxysilanes which behave as silylation reagents and also enhance the solubility of the silylated products in fluorocarbon solvents for preferred uses in fluorous phase synthesis. Generally, and preferably, the fluoroalkylsiloxysilanes according to the present invention are compounds designated by

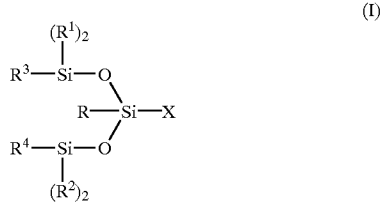

formula I:

In Formula I, $R^1$ and $R^2$ are independently selected from hydrogen or lower alkyl groups of from about 1 to 5 carbon atoms and are both preferably $CH_3$. $R^3$ is $R^1R^5$ where $R^5$ is any branched or straight chain perfluoroalkyl preferably of from about 1 to 25 carbon atoms and most preferably of from about 1 to 5 carbon atoms. $R^4$ is $R^1R^6$ where $R^6$ is any branched or straight chain perfluoroalkyl preferably of from about 5 to 25 carbon atoms and preferably from about 5 to 10 carbon atoms. As noted above, each $R^1$ or $R^2$ group on Si or in $R^3$ or $R^4$ may be the same or different within the compound. It is preferred that the total number of fluorine atoms in $R^3$ and $R^4$ is at least about fourteen. R is generally any linear or branched alkyl group, preferably a lower alkyl of from about 1 to 6 carbon atoms, more preferably an alkyl group of about 1 to 3 carbon atoms, and most preferably a methyl group. X is a hydrolyzable group or atom, preferably a halogen, such as chlorine or bromine, or a dimethylamino group, and most preferably chlorine.

For example, a preferred silylation reagent according to the present invention is a compound according to formula I in which R=methyl; X=chlorine; and $(R^1)_2=(R^2)_2=$ $(CH_3)_2$; $R^3=R^4=(CH_2)_2(CF_2)_5CF_3$. Such a compound is represented by formula II.

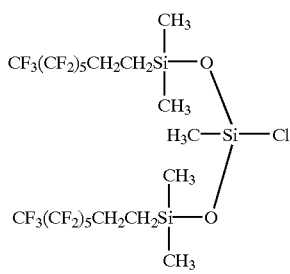

(II)

Compounds according to formula I behave as silylation reagents due to the presence of a hydrolyzable Si—X bond. Additionally, the presence of at least about fourteen fluorine atoms makes the compounds generally soluble in the fluorous phase. As a result, the silylated product may be more easily extracted into the fluorous phase and thus isolated from the reaction mixture.

This invention also relates to a two-step process for producing the fluoroalkylsiloxysilanes represented by formula I. In general, the first step involves the reaction of an alkyldialkoxysilane, such as preferably methyldiethoxysilane, with an excess of a fluoroalkyl-substituted silane, thereby substituting the alkoxy, preferably ethoxy, groups for fluoroalkylsiloxy substituents. In the second step, a silyl-hydride is converted to the desired hydrolyzable group by, as preferred non-limiting examples, chlorination or bromination.

This reaction sequence thus provides for the ability to synthesize a variety of fluoroalkylsiloxysilane compounds according to the present invention because the fluoroalkyl and hydrolyzable substituents are introduced to the silane in different steps.

As an example, the process to produce preferred compound II is illustrated. In the first step, equation III, methyldiethoxysilane is reacted with an excess of tridecafluorooctyldimethylchlorosilane to produce the intermediate product, bis(tridecafluorooctyldimethylsiloxy)methylsilane, as well as bis(tridecafluorooctyl)tetramethyldisiloxane as a byproduct.

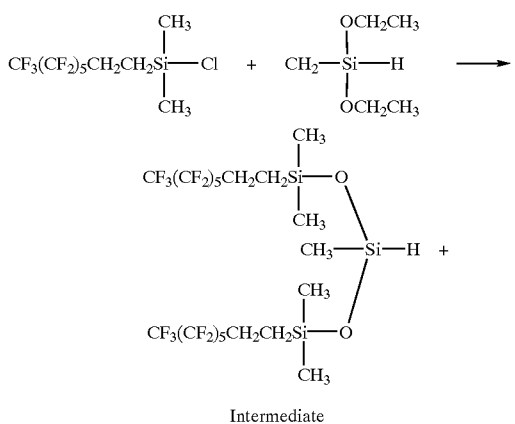

Intermediate (III)

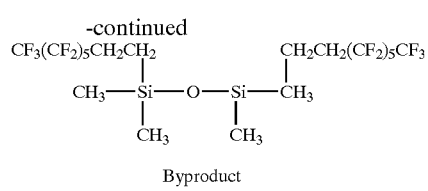

Byproduct

In the second step, illustrated by equation IV, the intermediate in equation (III) is reacted with chlorine gas to yield the desired silane of compound (II) and HCl as a byproduct.

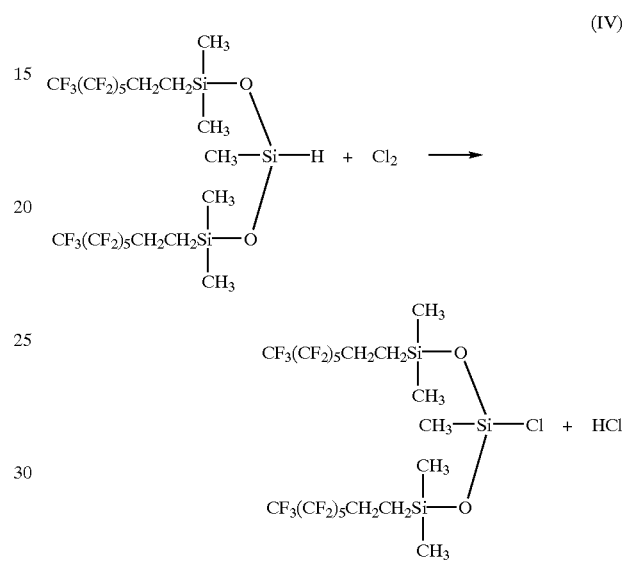

(IV)

The invention will be further illustrated in accordance with the following non-limiting example:

EXAMPLE 1

A 3 liter, 3-necked round bottom flask equipped with a condenser, addition funnel and agitator was charged with 881 g (2 moles) of tridecafluorooctyldimethylchlorosilane, 33.6 g (0.25 moles) of methyldiethoxysilane and 300 ml of methylene chloride. Water in an amount of 2.25 g was added dropwise over 5 minutes. The mixture was stirred for about 30 minutes, at which time the mixture became slightly hazy. A second portion of 2.25 g water was added and the mixture was stirred until it became a single phase. A volume of water equal to the flask contents was then added and the mixture was stirred for 10 minutes. After separation of the layers using a separatory funnel, the water layer was discarded. Two more washes with water were performed. The non-aqueous material was returned to the original reaction flask and an equal volume of water was added. Solid sodium bicarbonate was added with stirring until $CO_2$ evolution ceased. The clear bottom layer was then distilled through a 1 meter packed column. After removing methylene chloride, a forecut of bis(tridecafluorooctyl)tetramethyldisiloxane was removed (boiling point was 130° C./4 mm). The intermediate bis(tridecafluorooctyldimethylsiloxy)methylsilane (molecular weight MW of 738.33) was then recovered (boiling point of 136° C./3 mm, yield: 56 g of 88%). The specific gravity was measured to be 1.415 at 25° C. A characteristic IR absorption band was observed at ca 2154 nm.

EXAMPLE 2

A 250 ml 3-necked flask equipped with a cooling bath, magnetic stirrer, pot thermometer, addition funnel and condenser was charged with bis(tridecafluorooctyldimethylsiloxy)methylsilane formed in Example 1 and 50 ml of carbon tetrachloride. The mixture was cooled to the temperature range of −14° C. to −10° C. Chlorine was introduced into the solution with a simultaneous nitrogen sparge to remove the HCl byproduct as it formed. Chlorine was added until the solution became pale yellow. The pale yellow color disappeared as the solution warmed to 5° C. and the nitrogen sparge was continued. The mixture was distilled to obtain the product, bis(tridecafluoro-1,1,2,2-tetrahydrooctyldimethylsiloxy)methylchlorosilane (molecular weight MW of 921.06) with a boiling point of 122-6° C. at 1.6 mm. The specific gravity at 32° C. was 1.436.

This invention fulfills a need in the art for silylation reagents which enhance the solubility of the resulting silylated compound in fluorocarbon solvents, thus allowing for the separation of the silylated reaction product into the fluorous phase. These silane compounds thus accomplish two synthetic goals simultaneously: protecting the fragile protic hydrogen groups and providing for the straightforward separation of the ultimate reaction product through fluorous phase extraction.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A fluoroalkylsiloxysilane compound of formula I

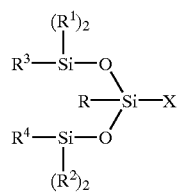

(I)

wherein $R^1$ and $R^2$ are independently selected from the group consisting of hydrogen and lower alkyl groups of from about 1 to 5 carbon atoms; $R^3$ is $R^1R^5$ wherein $R^5$ is any branched or straight chain perfluoroalkyl of from about 1 to 25 carbon atoms; $R^4$ is $R^1R^6$ wherein $R^6$ is any branched or straight chain perfluoroalkyl of from about 5 to 25 carbon atoms; R is selected from the group consisting of linear and branched alkyl groups; and X is a hydrolyzable group or atom.

2. The compound according to claim 1, wherein R is selected from the group consisting of linear or branched lower alkyl groups of from about 1 to 6 carbon atoms.

3. The compound according to claim 2, wherein R is an alkyl group selected from the group consisting of methyl, ethyl and isopropyl.

4. The compound according to claim 1, wherein X is a halogen atom.

5. The compound according to claim 4, wherein X is selected from the group consisting of chlorine and bromine.

6. The compound according to claim 1, wherein X is a dimethylamino group.

7. The compound according to claim 1, wherein $(R^1)_2$=$(R^2)_2$=$CH_3$; $R^3$=$R^4$=$(CH_2)_2(CF_2)_5CF_3$; R=methyl and X=chlorine, designated formula II

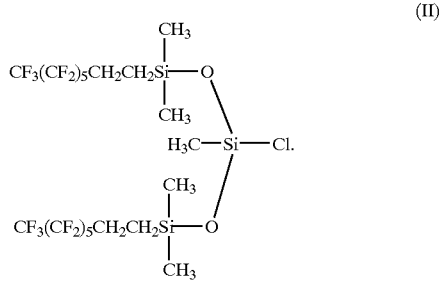

(II)

8. A process for producing a compound of formula I,

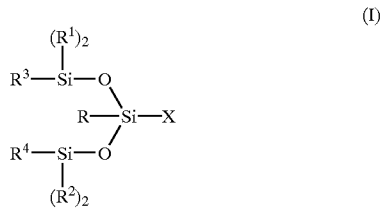

(I)

wherein $R^1$ and $R^2$ are independently selected from the group consisting of hydrogen and lower alkyl groups of from about 1 to 5 carbon atoms; $R^3$ is $R^1R^5$ wherein $R^5$ is any branched or straight chain perfluoroalkyl of from about 1 to 25 carbon atoms; $R^4$ is $R^1R^6$ wherein $R^6$ is any branched or straight chain perfluoroalkyl of from about 5 to 25 carbon atoms; R is selected form the group consisting of linear and branched alkyl groups; and X is a hydrolyzable group or atom, comprising:
(a) reacting an alkyldialkoxysilane with a perfluoroalkyl-substituted silane to produce a perfluoroalkyl-substituted dialkylsiloxyalkylsilane intermediate;
(b) reacting the intermediate with halogen.

9. The process according to claim 8, for producing the compound of formula II,

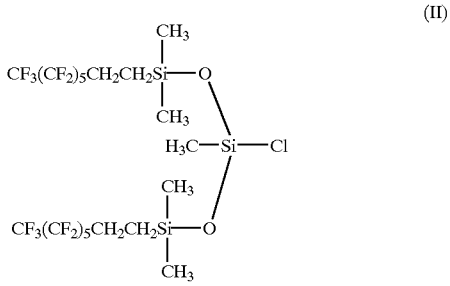

(II)

comprising:
(a) reacting methyldiethoxysilane with tridecafluorodimethylchlorosilane to produce a bis(tridecafluorooctyldimethylsiloxy)methylsilane intermediate;
(b) reacting the intermediate with halogen.

* * * * *